(12) United States Patent
Fink et al.

(10) Patent No.: US 6,769,770 B2
(45) Date of Patent: *Aug. 3, 2004

(54) COMPUTER-BASED 3D VISUAL FIELD TESTING WITH PERIPHERAL FIXATION POINTS

(75) Inventors: Wolfgang Fink, Montrose, CA (US); Alfredo A. Sadun, San Marino, CA (US)

(73) Assignee: California Institute of Technology, Pasadena, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 10/178,966

(22) Filed: Jun. 25, 2002

(65) Prior Publication Data

US 2003/0020873 A1 Jan. 30, 2003

Related U.S. Application Data

(63) Continuation-in-part of application No. 09/820,283, filed on Mar. 27, 2001, now Pat. No. 6,578,966.
(60) Provisional application No. 60/192,645, filed on Mar. 27, 2000, provisional application No. 60/204,362, filed on May 15, 2000, provisional application No. 60/250,901, filed on Dec. 1, 2000, and provisional application No. 60/251,957, filed on Dec. 7, 2000.

(51) Int. Cl.[7] .................................................. A61B 3/02
(52) U.S. Cl. ...................................................... 351/239
(58) Field of Search ................................ 351/211, 222, 351/223, 237, 239, 240, 242, 243, 246

(56) References Cited

U.S. PATENT DOCUMENTS

| | | | | |
|---|---|---|---|---|
| 5,589,897 A | * | 12/1996 | Sinclair et al. | 351/223 |
| 5,892,570 A | | 4/1999 | Stevens | |
| 6,260,970 B1 | * | 7/2001 | Horn | 351/246 |
| 6,513,931 B1 | * | 2/2003 | Torrey et al. | 351/243 |
| 6,572,229 B2 | * | 6/2003 | Wei | 351/211 |

FOREIGN PATENT DOCUMENTS

| | | |
|---|---|---|
| EP | 0307604 A2 | 3/1989 |
| WO | WO-96/34555 A1 | 11/1996 |
| WO | WO-01/72212 A1 | 10/2001 |

OTHER PUBLICATIONS

PCT International Search Report dated Aug. 6, 2001 from related International Application No. PCT/US01/09821 filed Mar. 27, 2001.

PCT Written Opinion dated Feb. 26, 2002 from related International Application No. PCT/US01/09821 filed Mar. 27, 2001.

PCT International Preliminary Examination Report dated May 24, 2002 from related International Application No. PCT/US01/09821 filed Mar. 27, 2001.

\* cited by examiner

*Primary Examiner*—George Manuel
(74) *Attorney, Agent, or Firm*—Christie, Parker & Hale LLP

(57) ABSTRACT

A method and apparatus for electronically performing a visual field test for a patient. A visual field test pattern including a peripheral fixation point is displayed to the patient on an electronic display device and the patient's responses to the visual field test pattern are recorded. A visual field representation is generated from the patient's responses. The visual field representation is then used as an input into a variety of diagnostic processes. In one embodiment of the invention, a series of visual test patterns of varying contrast levels or colors are presented to a patient in order to construct a three-dimensional visual field representation wherein contrast sensitivity is plotted as the Z-axis.

44 Claims, 15 Drawing Sheets

COMPUTER-BASED 3D VISUAL FIELD TESTING WITH PERIPHERAL FIXATION POINTS

CROSS-REFERENCE TO RELATED APPLICATION

The present application is a continuation-in-part of copending U.S. patent application Ser. No. 09/820,283, filed Mar. 27, 2001, now issued as U.S. Pat. No. 6,578,966, which claims the benefit of U.S. Provisional Application No. 60/192,645 filed on Mar. 27, 2000, U.S. Provisional Application No. 60/204,362 filed on May 15, 2000, U.S. Provisional Application No. 60/250,901 filed on Dec. 1, 2000, and U.S. Provisional Application No. 60/251,957 filed on Dec. 7, 2000, each of which are expressly incorporated by reference as though fully set forth in full herein.

STATEMENT REGARDING FEDERALLY SPONSORED RESEARCH OR DEVELOPMENT

The U.S. Government has certain rights in this invention pursuant to grant PHY-9722428 awarded by the National Science Foundation.

BACKGROUND OF THE INVENTION

This invention relates generally to the field of medical instrumentation and more specifically to detection of defects of the retina, the optic nerve, and the brain's visual pathways.

A large number of medical ailments manifest themselves as defects in a patient's visual field. Patients suffering from macular degeneration, anterior ischemic optic neuropathy (AION), glaucoma, optic neuritis, detached retina, macular edema, central or branch retinal artery occlusion, some genetic impairments, and brain tumors may experience losses in visual acuity and visual field.

Non-invasive methods to measure a patient's visual field have been developed. For example, perimetry and campimetry provide information pertaining to the borderline between seeing and non-seeing areas within a patient's visual field.

Visual field tests employing visual field test patterns, such as an Amsler grid, have been developed to give a qualitative analysis of a patient's visual field. However such tests do not provide data of sufficient resolution or precision to perform a quantitative analysis of a patient's condition.

Recent developments of testing methods using visual field test patterns have included adjusting a patient's perception of the contrast levels within a visual field test pattern. For example, a method disclosed in U.S. Pat. No. 4,818,091, the disclosure of which is hereby incorporated by reference, requires the use of eyeglasses with polarized lenses to adjust the apparent contrast level of an Amsler grid.

These methods suffer from a variety of problems. Some methods require a patient to endure a long and boring testing process during which time the patient's concentration may lag because of fatigue. Other methods, while capable of being quickly performed, do not provide the spatial and contrast resolution required for high quality quantitative analysis.

Therefore, a need exists for a method that is quicker, simpler and more revealing than existing methods for characterizing the visual field. The present invention meets such need.

SUMMARY OF THE INVENTION

A method and apparatus for electronically performing a visual field test for a patient is provided. A visual field test pattern including a peripheral fixation point is displayed to the patient on an electronic display device and the patient's responses to the visual field test pattern are recorded. A visual field representation is generated from the patient's responses. The visual field representation is then used as an input into a variety of diagnostic processes. In one embodiment of the invention, a series of visual field test patterns of varying contrast are presented to a patient in order to construct a three-dimensional visual field representation wherein contrast sensitivity is plotted as the Z-axis.

In one aspect of the invention, a visual field measurement apparatus includes an electronic visual field test pattern display device for display of visual field test patterns including a peripheral fixation point to a patient, a patient response input device for recording a patient's response to a visual field test pattern, and a tester operably coupled to both for conducting the visual field measurement.

A patient views a visual field test pattern and selects areas in the visual field test pattern where the visual field test pattern is missing or distorted. The patient selects these visual field test pattern areas using a touch screen mounted on the electronic display device. A series of visual field test patterns of differing contrasts are presented to the patient and the patient's responses are recorded.

A visual field representation generator operably coupled to the tester generates a visual field representation using the patient's responses. The visual field representation is used in a variety of diagnostic processes.

In another aspect of the invention, a distributed visual field measurement system is created using a tester Web server operably coupled to a browser via the Internet. The tester Web server serves pages to the browser implementing a visual field measurement system.

In another aspect of the invention, visual field representations are correlated with known causes of visual field defects and stored in a diagnostic database operably coupled to a diagnostic server accessible via the Internet. A clinician sends a visual field representation to the diagnostic server. The diagnostic server uses an AI engine to determine a diagnosis using the visual field representation.

BRIEF DESCRIPTION OF THE DRAWINGS

These and other features, aspects, and advantages of the present invention will become better understood with regard to the following descriptions and accompanying drawings where.

DETAILED DESCRIPTION OF THE INVENTION

Figure 1:
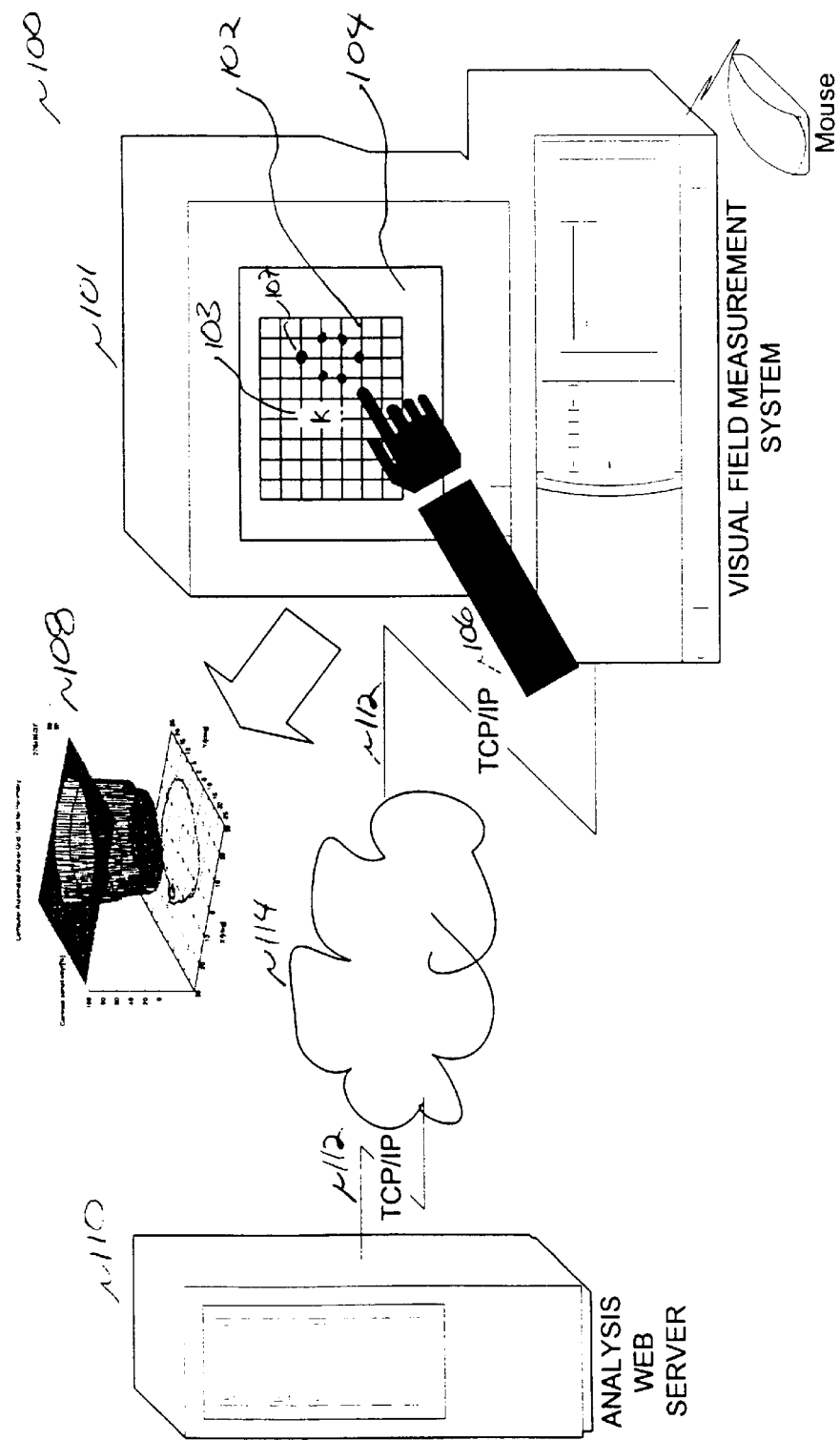
FIG. 1 is a depiction of an embodiment of a visual field measurement system according to the present invention.

FIG. 1 is a depiction of an embodiment of a visual field measurement system according to the present invention. A visual field measurement system 100 comprises a computer system with an electronic display 101 upon which a visual field test pattern 102 including a variable fixation point 103 is displayed. A patient response input device such as a touchscreen 104 is used to record for a patient's 106 response to the displayed visual field test pattern.

In operation, examination of a patient occurs in an examination room with a controlled ambient brightness. The patient is positioned in front of the electronic display at a fixed distance thus determining the angle of the patient's visual field. The patient's eye not under examination is covered with an eye-cover.

A visual field test pattern is displayed at a preselected contrast and angular resolution to the patient using the electronic display. The patient responds to the display of the visual field test pattern by selecting locations 107 within the field test pattern between areas where the patient clearly sees the visual field test pattern and areas where the patient is having difficulty seeing the visual field test pattern. The patient's responses are recorded and a visual field representation 108 is generated for diagnostic purposes.

In another embodiment of a visual field measurement system according to the present invention, analysis of the patient's responses or the visual field representation occurs at a remote analysis Web server site 110. The visual field measurement system is operably coupled to the Web server via communication links 112 adapted for communications using Transmission Control Protocol/Internet Protocol (TCP/IP) protocols such as Hyper Text Transfer Protocol (HTTP) via a communications network such as a Local Area Network (LAN) or a Wide Area Network (WAN) exemplified by Internet 114. The analysis Web server receives the patient's responses or the visual field representation and makes a comparison to previously received patients' responses or visual field representations. From the comparison, a diagnosis can be made of the patient's medical condition.

FIGS. 15a, 15b, 15c, and 15d are depictions of visual field test patterns with peripheral fixation points in accordance with an exemplary embodiment of the present invention. Visual field test patterns with peripheral fixation points allow testing for diseases that manifest themselves in the peripheral vision of a patient, such as glaucoma and for testing of larger visual fields with higher eccentricities. Visual field test pattern 1500 includes peripheral variable fixation point 1502 in an upper left-hand corner of visual field test pattern 1500. Configured in this manner, visual field test pattern 1500 permits testing of a lower right quadrant of a patient's visual field. Visual field test pattern 1504 includes peripheral variable fixation point 1506 in an upper right-hand corner of visual field test pattern 1504. Configured in this manner, visual field test pattern 1504 permits testing of a lower left quadrant of a patient's visual field. Visual field test pattern 1508 includes peripheral variable fixation point 1510 in a lower left-hand corner of visual field test pattern 1508. Configured in this manner, visual field test pattern 1508 permits testing of an upper right quadrant of a patient's visual field. Visual field test pattern 1512 includes peripheral variable fixation point 1514 in a lower left-hand corner of visual field test pattern 1512. Configured in this manner, visual field test pattern 1512 permits testing of an upper left quadrant of a patient's visual field. In another embodiment of a visual field test pattern in accordance with an exemplary embodiment of the present invention, a plurality of peripheral fixation points are included in the visual field test pattern.

Figure 2:
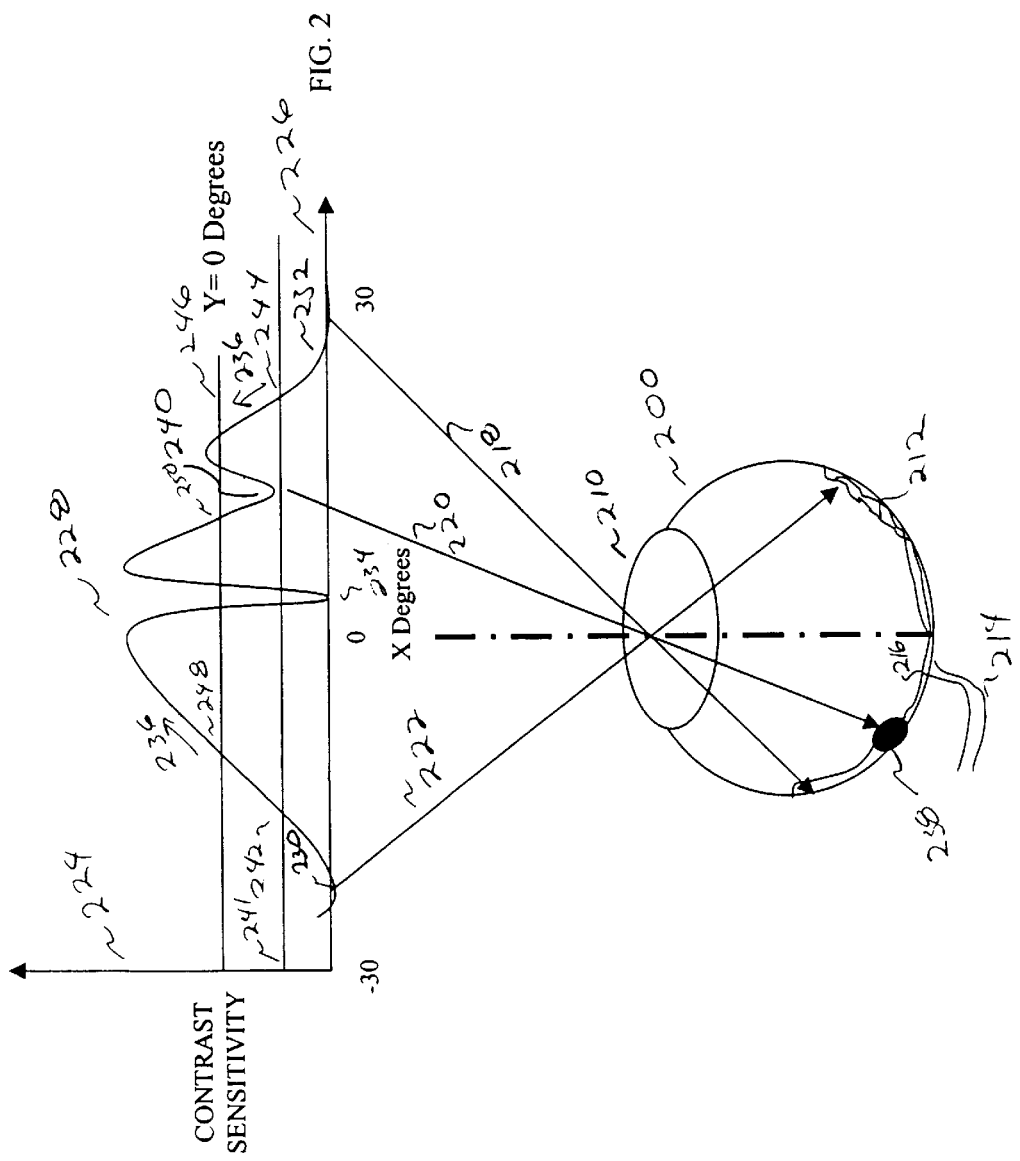
FIG. 2 is a depiction of a cross section of an eye showing retinal sensitivity within a retina's visual field.

FIG. 2 is a depiction of a cross section of an eye showing retinal sensitivity within a retina's visual field. An eye 200 partially comprises a cornea 210 and a retina 212. The cornea focuses light rays 218, 220, and 222 onto the retina. Cells within the retina transduce the incoming light rays into signals via a photochemical reaction. The resultant signals are transported from the retina to the brain for processing by an optic nerve 214. The optic nerve is coupled to the retina at the optic disk 216. The optic disk is not sensitive to light.

The contrast sensitivity of the retina varies from the perimeter of the retina to the center. The retina's contrast sensitivity is highest at the retina's center and lowest at the retina's perimeter. When plotted along an Y axis 224 versus the eccentricity of the retina's visual field in Degrees along an X axis 226, the contrast sensitivity of the retina describes a contrast sensitivity curve 228 with several local maxima and minima.

Two contrast sensitivity curve local minima are located on the portion of the contrast sensitivity curve corresponding to the retina's perimeter of the retina 230 and 232. One contrast sensitivity curve local minimum 234 is located at the portion of the contrast sensitivity curve associated with the retina's optical disk. As one moves from the perimeter of the retina to the center of the retina, the sensitivity of the retina increases 236.

Defects in the retina may cause the retina to lose its contrast sensitivity 240 either partially or totally. This loss in contrast sensitivity translates into defects in the visual field. Thus, defects in the retina can be detected by measuring the retina's visual field. Additionally, defects in the optic nerve or in a patient's ability to process visual information in the brain may also cause defects in the visual field.

The contrast sensitivity of the retina and pathways can be measured by presenting visual field test patterns of differing contrast to a patient. For example, if a first visual field test pattern has a high contrast level, as represented by a first constant contrast sensitivity 241, the retina detects the visual field test pattern at locations, 242 and 244, on the contrast sensitivity curve corresponding to locations on the retina close to the retina's perimeter.

If a second visual field test pattern has a low contrast level, as represented by a second constant contrast sensitivity line 246, the retina detects the second visual field test pattern at contrast sensitivity curve locations, 248 and 250, corresponding to locations on the retina close to the retina's center. In this case, the second test pattern's contrast is too low to be detected by the defective portion of the retina 238.

Figure 3:
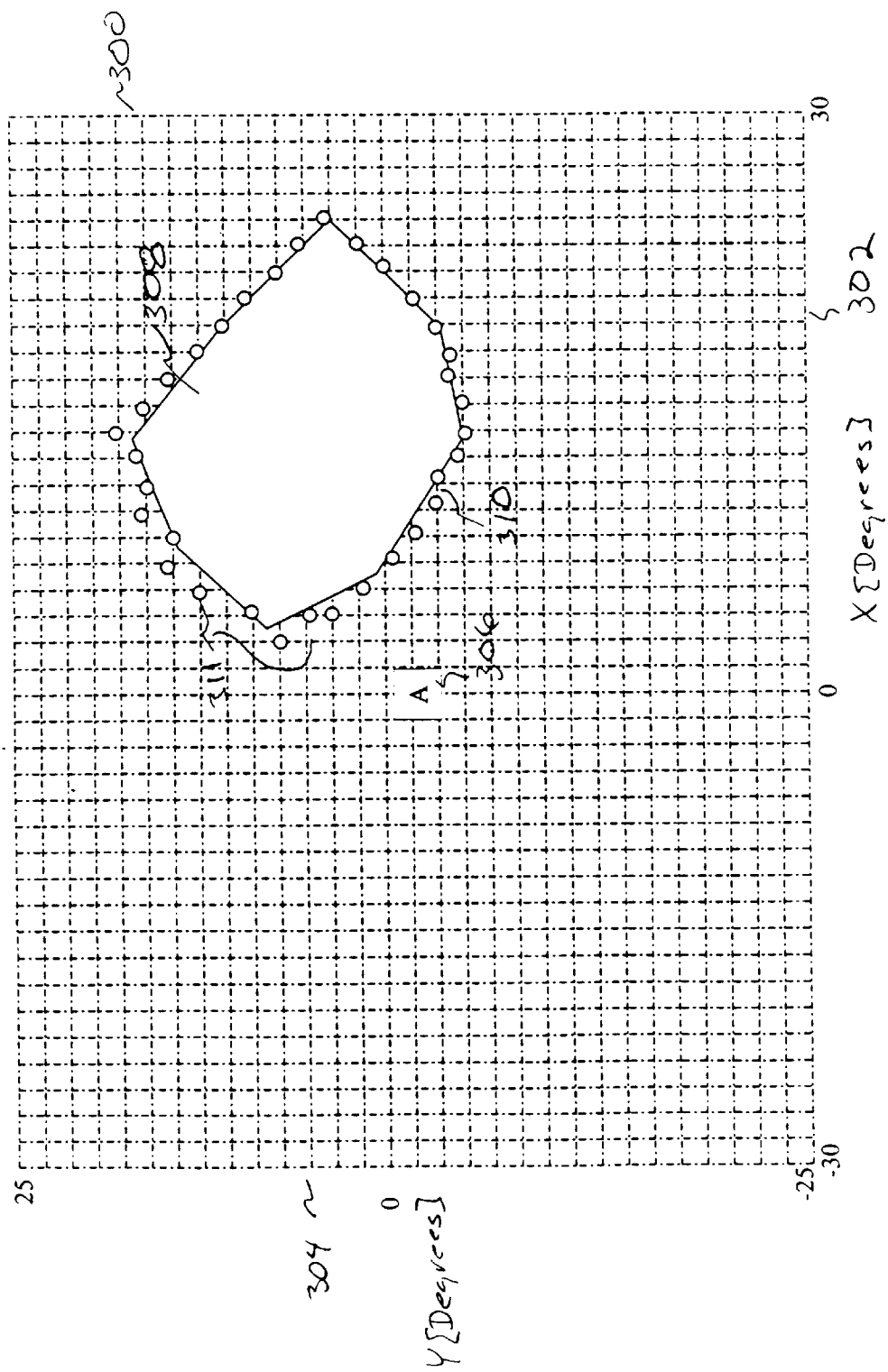
FIG. 3 is a depiction of an embodiment of a visual field test pattern at a low contrast level used to measure a visual field according to an embodiment of the present invention.

FIG. 3 is a depiction of an embodiment of a visual field test pattern at a low contrast level used to measure a visual field according to an embodiment of the present invention. A visual field measurement system 100 (FIG. 1) presents the visual field test pattern to a patient using an electronic display 101 (FIG. 1). The visual field test pattern includes a series of vertical lines and horizontal lines substantially orthogonal to one another thus creating a rectilinear grid 300. The lines of the grid are distributed along an X axis 302 and a Y axis 304 such that when a patient views the visual field test pattern presented on the electronic display, the lines create a grid with a grid spacing of at least 1.0 arc minutes within the patient's visual field. The exact grid spacing is variable and dependent on testing conditions and clinician preference.

The appearance of a visual field defect is dependent on the type of defect present in the retina, optic nerve, or patient's visual processing abilities. In this case, a defect in the visual field is presented as an area 308 where the grid is not visible to the patient. The patient touches the electronic display at a perimeter location 310 corresponding to an edge of the area of the visual defect. A location where the patient touches the electronic display is sensed by a touch screen 102 (FIG. 1) and recorded. The patient continues touching the perimeter of the area of the visual field defect describing a series of rectilinear locations recorded as the patient's response to the visual field test pattern. These rectilinear locations define a perimeter for the visual field defect at a single contrast level.

Figure 4:
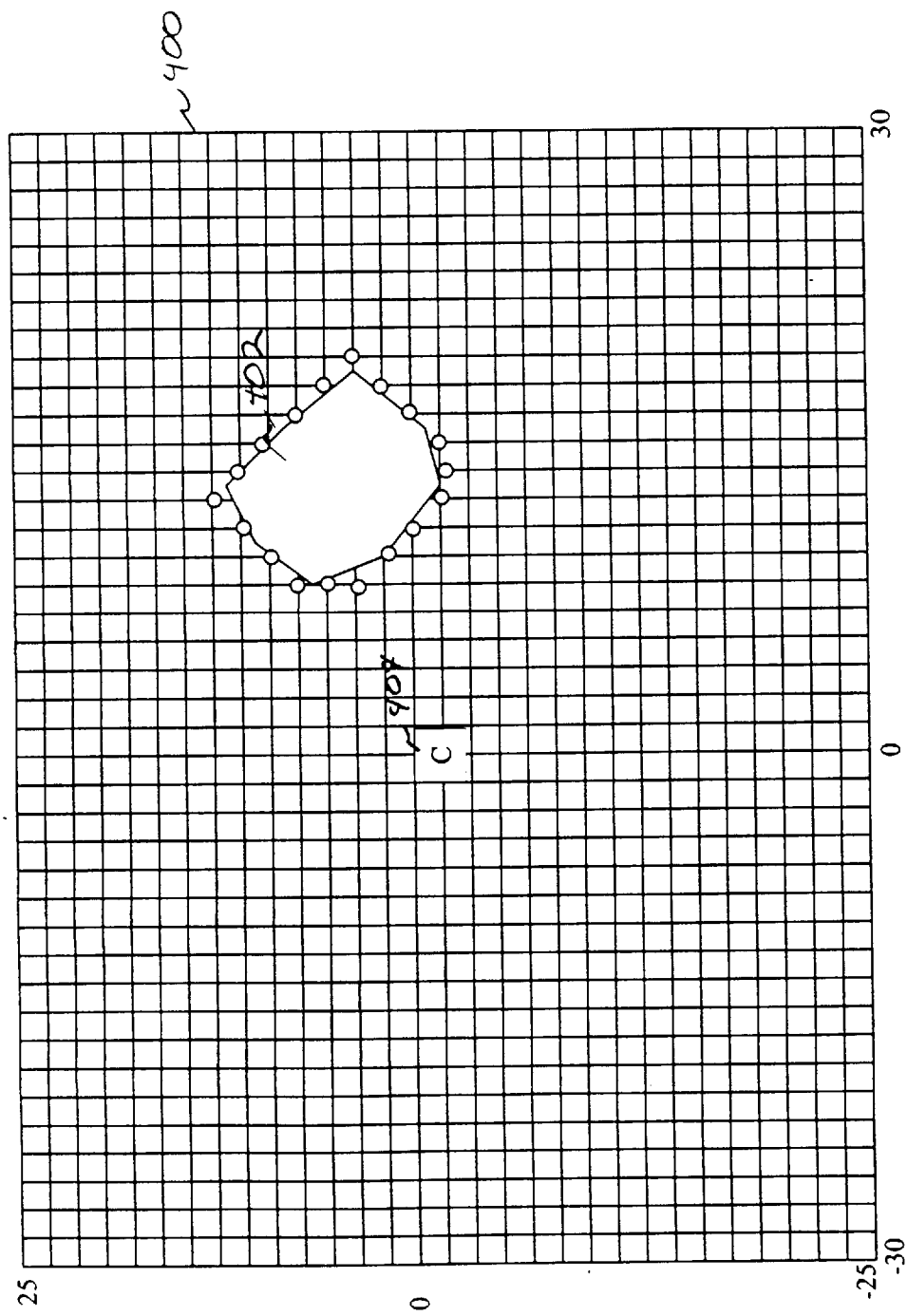
FIG. 4 is a depiction of an embodiment of a visual field test pattern at a high contrast level used to measure a visual field defect according to an embodiment of the present invention.

FIG. 4 is a depiction of an embodiment of a visual field test pattern at a high contrast level used to measure a visual field defect according to an embodiment of the present invention. The high contrast visual field test pattern has the same overall configuration of the previously described low contrast visual field test pattern but the high contrast visual field test pattern is presented to the patient at a high contrast level.

The visual field measurement system presents the visual field test pattern to the patient and the patient's response to the visual field test pattern is recorded as previously described. This time however, the patient may perceive that the defect in the visual field has grown smaller because the visual field test pattern has a higher contrast level and is thus easier to see.

In another embodiment of a visual field test pattern according to the present invention, the visual field test pattern is a rectilinear grid known as an Amsler grid.

In another embodiment of a visual field test pattern according to the present invention, a fixation point is presented to the patient and the fixation point is varied during the time the visual field test pattern is presented to the patient. For example, the fixation point may be a displayed letter and the displayed letter is randomly and constantly changed during the time the visual field test pattern is being presented to the patient.

In another embodiment of a visual field test pattern according to the present invention, the visual field test pattern is varied slightly during the testing period in order to mitigate a Troxler effect. Varying the visual field test pattern is accomplished be either changing the display position of the visual test pattern on a display device or by causing the visual field test pattern to flicker at a frequency selected to mitigate the Troxler effect.

In another visual field test pattern in accordance with an exemplary embodiment of the present invention, the color of the elements included in the visual field test pattern, such as the previously described grid lines and fixation points, is varied. For example, the visual test pattern can be presented in a single color, such as red, and the contrast levels are varied for the visual test pattern in order to elicit a patient response. In another example, the color of a visual field test pattern is varied, such as first presenting a visual field test pattern in red and then presenting the visual field test pattern in green, in order to elicit a patient response. In another example, both the contrast levels and the color are varied in order to elicit a patient response.

Figure 5:
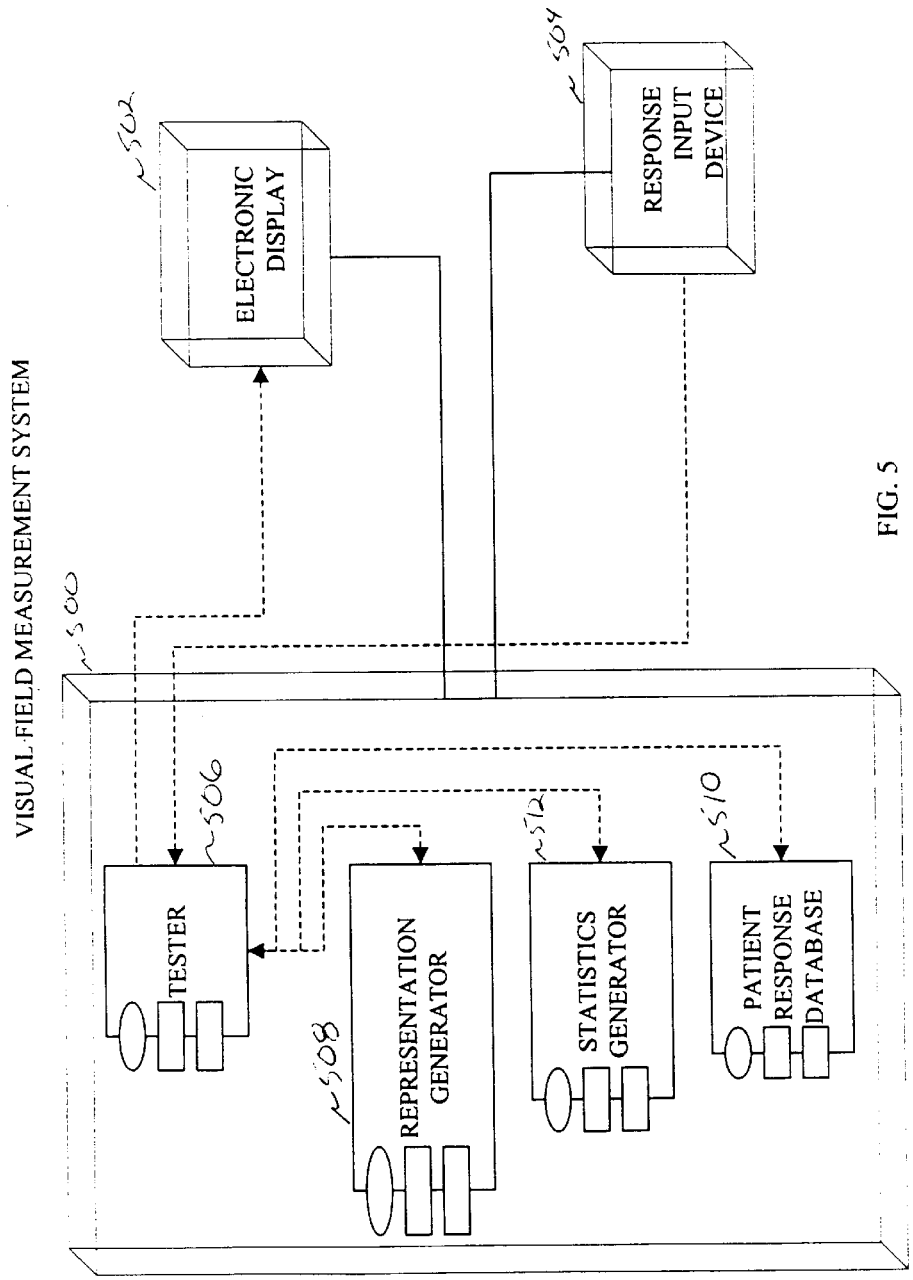
FIG. 5 is a deployment diagram of an embodiment of a visual field measurement system according to the present invention.

FIG. 5 is a deployment diagram of an embodiment of a visual field measurement system according to the present invention. A visual field measurement system comprises a central processor 500 operably coupled to an electronic display 502 and a patient response input device 504.

In one embodiment of a visual field measurement system, a personal computer is used with a conventional CRT display. The CRT display is modified with a touchscreen device so that a patient may simply touch the CRT display at the locations where the patient detects a change in the appearance of the visual field test pattern.

In another embodiment of a visual field measurement system, the touchscreen device is replaced by a pointing device, such as a trackball or mouse, operably coupled to a programmatically controlled cursor presented on the electronic display along with the visual field test pattern. The patient manipulates the cursor to outline the visual field defect.

In another embodiment of a visual field measurement system, the cursor is controlled through keyboard inputs.

In another embodiment of a visual field measurement system, a plurality of electronic displays and patient response input devices are operably coupled to a single central processor. In this case, a plurality of patients may be tested at a single time.

In other embodiments of visual field measurement systems, other electronic displays capable of displaying visual field test patterns at varying contrast levels are used such as projection screens, Liquid Crystal Displays (LCDs), plasma displays, etc.

The visual field measurement system further comprises software objects hosted by the central processor. The software objects include a tester 506 operably coupled to the electronic display and the patient response device. The tester generates visual field test patterns for display to the patient using the electronic display. The tester package receives patient response signals from the patient response input device and records patient responses generated from the patient response signals for use by a representation generator 508.

The representation generator accepts patient responses from the tester and generates a visual field representation from the patient response signals suitable for use in a diagnostic process.

In one embodiment of a visual field measurement system, the tester is operably coupled to a patient response database 510. The tester puts the patient response in the patient response database along with a patient identification and time and date information. A time series of stored patient responses taken over time from the same patient is then used to watch the progress of a patient's medical condition.

In another embodiment of a visual field measurement system, the tester puts visual field representations in the user response database. The stored visual field representations are used in the same manner as the patient responses as previously described.

In another embodiment of a visual field measurement system according to the present invention, the tester is operably coupled to a statistics generator 512. The statistics generator accepts patient responses or visual field representations and generates descriptive statistics useful for diagnostic purposes.

Figure 6:
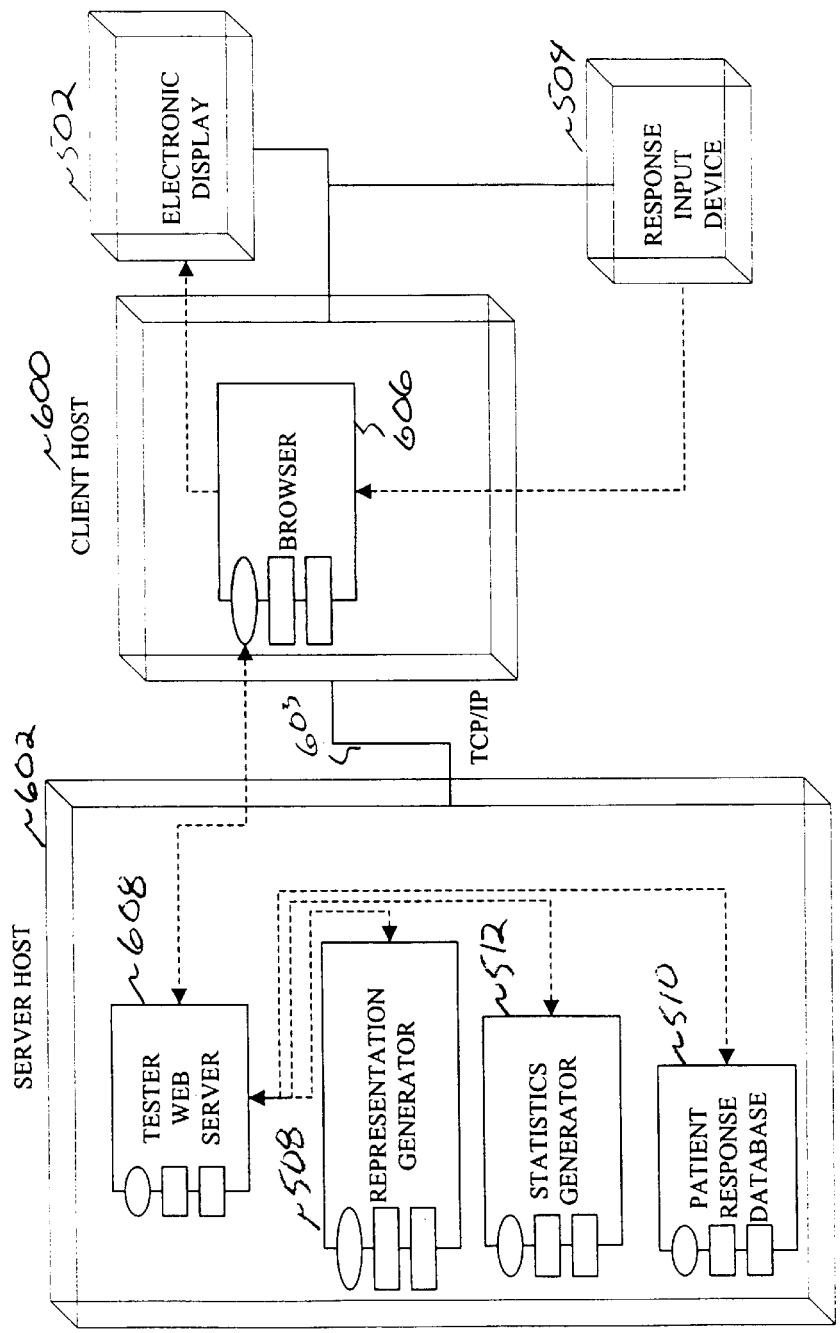
FIG. 6 is a deployment diagram of a Web based embodiment of a visual field measurement system according to the present invention.

FIG. 6 is a deployment diagram of a Web based embodiment of a visual field measurement system according to the present invention. A client host 600 is operably coupled to a server host 602 via a communications link 603 adapted for communications using TCP/IP. The client host is operably coupled to a previously described electronic display 502 and a previously described patient response input device 504. A browser 606 hosted by the client host is operably coupled to the electronic display and the patient response input device. The browser requests and receives Web pages from a tester Web server 608 hosted by the server host. The Web pages served from the tester Web server implement the previously described visual field measurement procedure.

The browser collects patient responses from the response input device and posts the results to the tester Web server. The tester Web server is operably coupled to a previously described representation generator 508, patient response database 510, and statistics generator 512. The tester Web server uses the representation generator to generate visual field representations from patient responses as previously described and incorporates the visual field representations into a Web page that is transmitted back to the browser for display.

Figure 7:
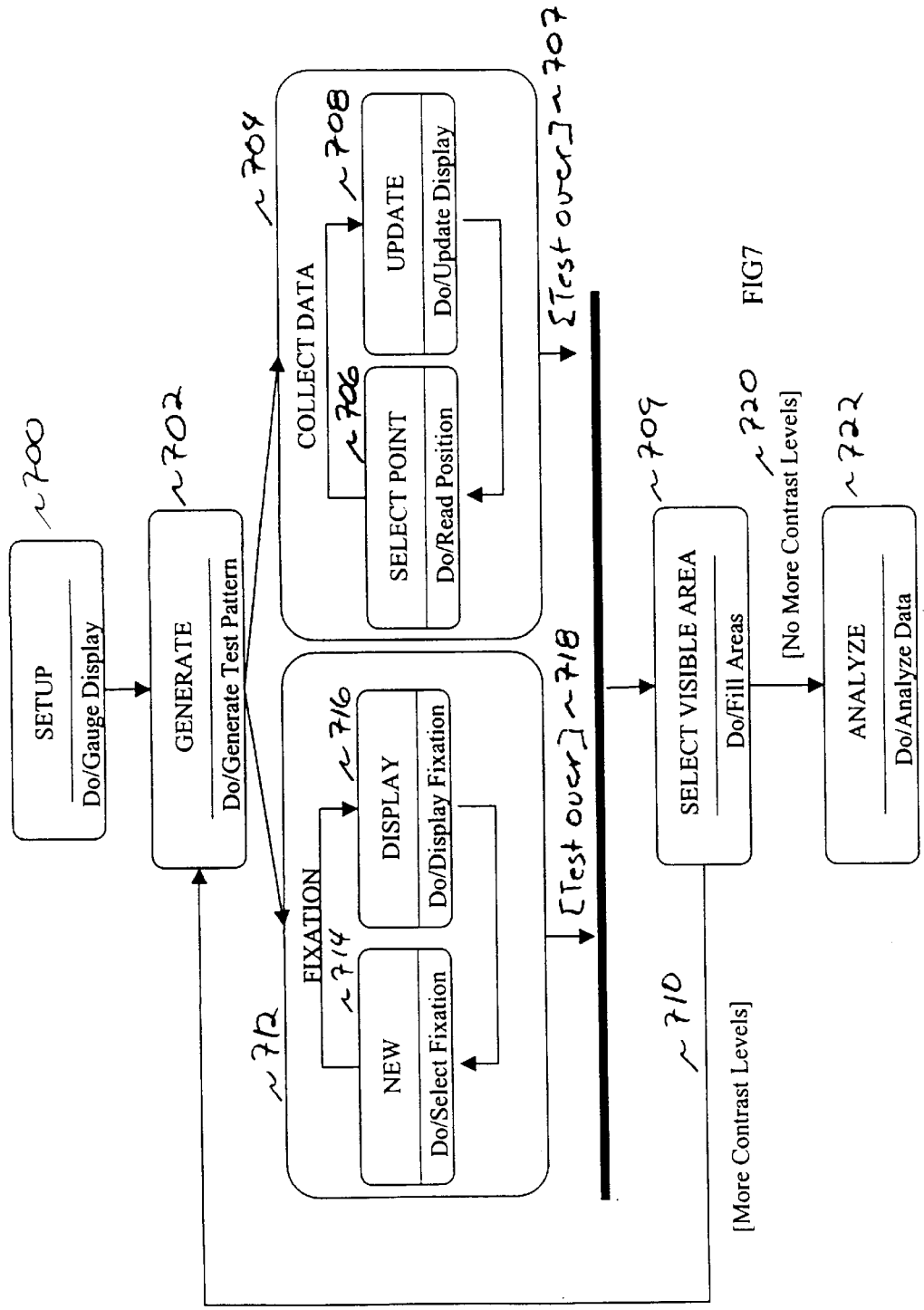
FIG. 7 is a state diagram for a tester object embodiment of a visual field measurement system according to the present invention.

FIG. 7 is a state diagram for a tester object embodiment of a visual field measurement system according to the present invention. A tester software object 506 (FIG. 5) performs a setup 700 of the electronic display including adjusting the size of the visual field test pattern based on the size of the electronic display and a distance between a patient and the electronic display. Patient information is collected for association with the patient response in the previously described patient response database.

A first contrast level is set and a visual field test pattern is generated 702 for the first contrast level. The visual field test pattern is presented to the patient and the collection of patient response signals from a previously described patient input device begins.

The tester collects data from the patient response input device by reading points 706 selected by the patient outlining the perimeter of any visual field defects observed by the patient. The tester updates 708 the electronic display by highlighting the points selected by the patient.

At the end of the test, a clinician or the patient selects an area of the visual field test pattern that the patient can see clearly 709. This indicates to the tester whether the areas of the visual field test pattern within the enclosed perimeter outlined by the patient are areas where the patient can see or not see the visual field test pattern. For example, in the previously described high contrast visual field test pattern 400 (FIG. 4), a patient cannot see the visual field test pattern within the area of the visual defect 402 (FIG. 4). In this case, the clinician or patient selects an area of the visual field test pattern outside of the visual defect area to indicate that the patient can see that portion of the visual field test pattern.

The tester determines if there are more contrast levels to test 710 and returns to the visual field test pattern generation and contrast setting state 702 and the collect data state 704 until no more contrast levels are needed.

In another embodiment of a visual field measurement system according to the present invention, the screen update at update state 708 includes updating a cursor location indicating the position of a displayed cursor responsive to a user input device such as a pointing device or track ball.

In another embodiment of a visual field measurement system according to the present invention, a plurality of visual field test patterns with varying contrast levels are presented to a patient in order of decreasing or increasing contrast levels.

In another embodiment of a visual field measurement system according to the present invention, a plurality of visual field test patterns with varying contrast levels are presented to a patient in random order with respect to the varying contrast levels.

In another embodiment of a visual field measurement system according to the present invention, the visual field test pattern contains a variable fixation point as previously described. In this case, the tester simultaneously generates new fixation points 712 while the tester is collecting patient responses. The tester constantly determines a new 714 fixation point and displays 716 the new fixation point until the test is over 718.

If no more visual field test patterns for new contrast levels are to be generated 720, the tester moves into an analyze state where the collected data is analyzed for diagnostic purposes.

Figure 8:
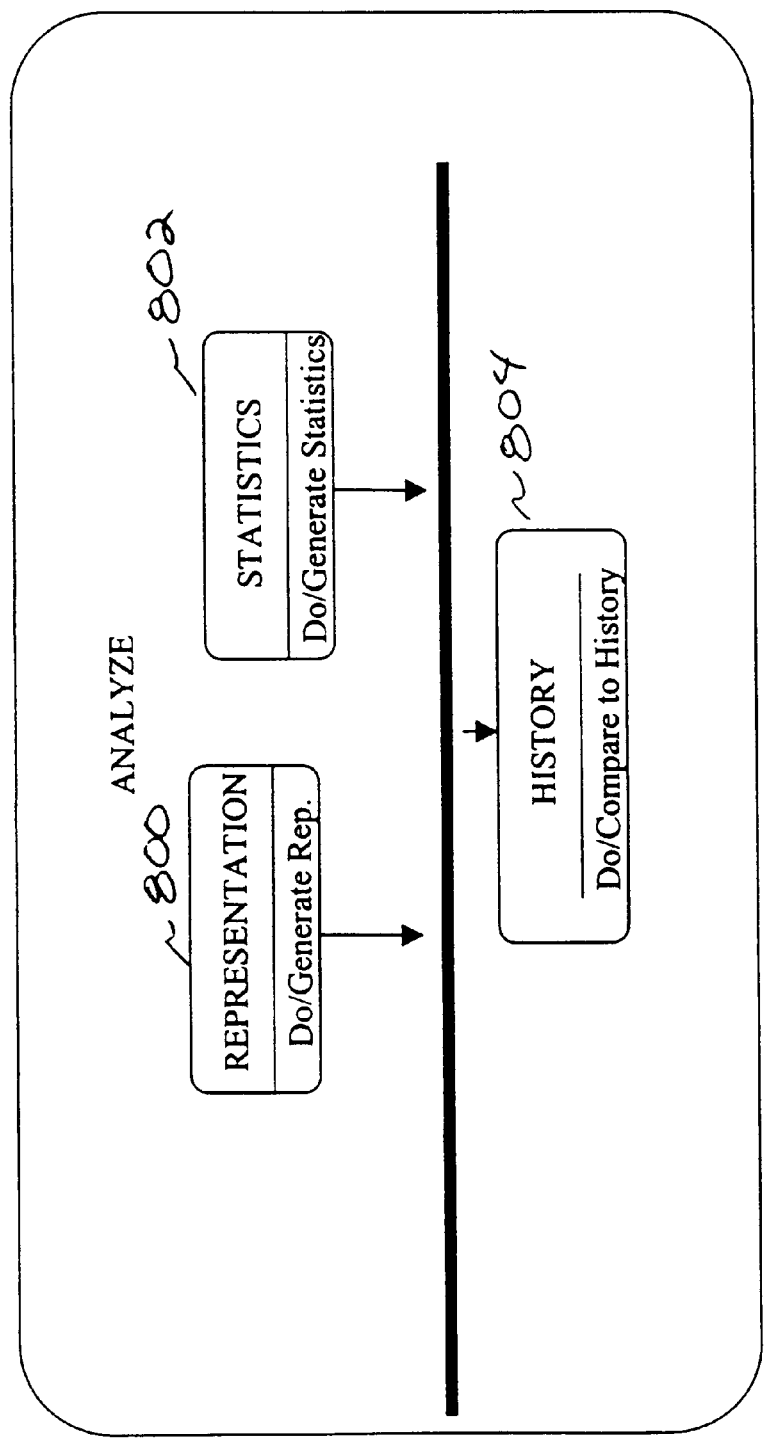
FIG. 8 is a state diagram for an analysis state embodiment of visual field measurement system according to the present invention.

FIG. 8 is a state diagram for an analysis state embodiment of visual field measurement system according to the present invention. In the analyze state, the tester generates a to be described visual field representation using the previously described patient response data 800. The visual field representation can be saved for use in further diagnostic processes or can be displayed directly to a clinician for diagnostic purposes.

Figure 9:
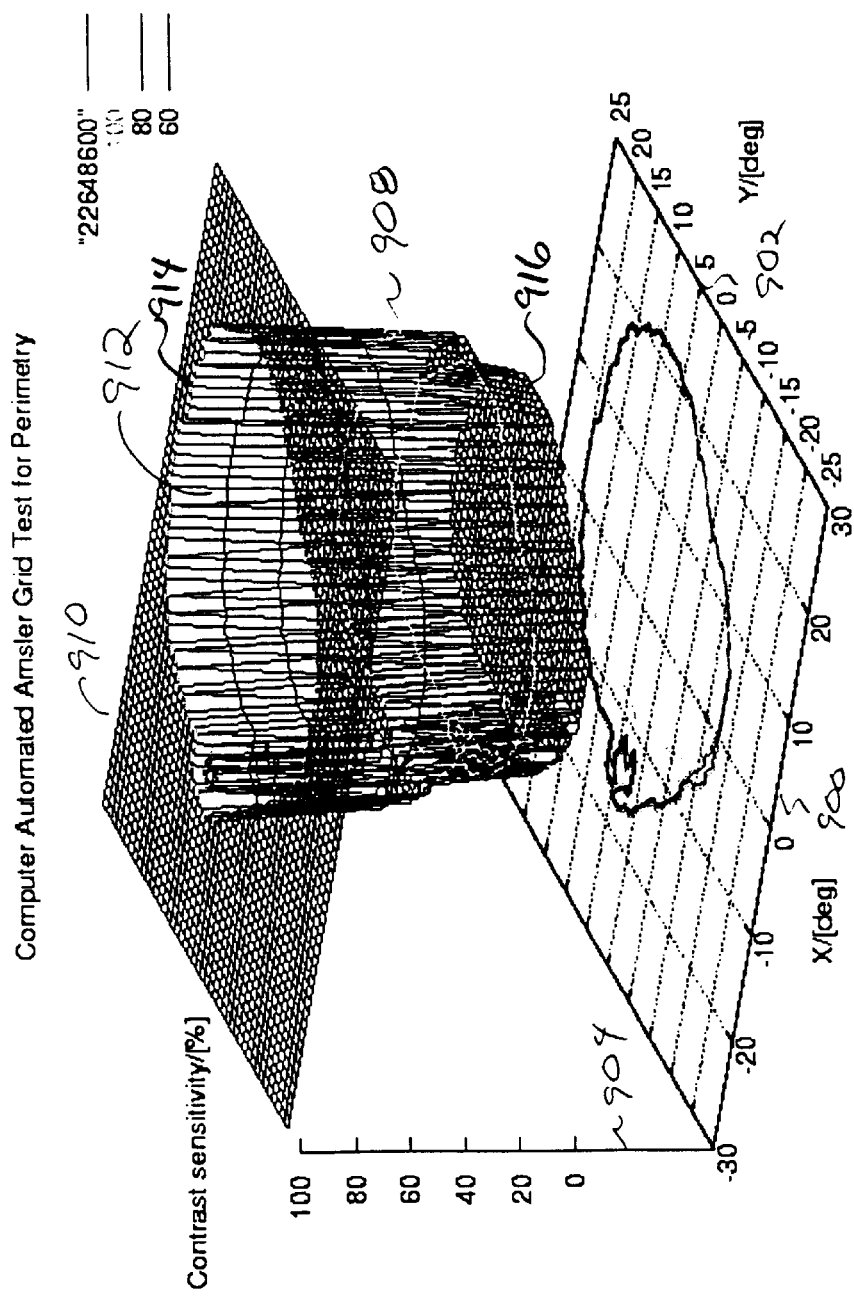
FIG. 9 is an exemplary visual field representation for a patient with "dry" macular degeneration generated by an embodiment of a visual field measurement system according to the present invention from a patient response.

FIG. 9 is an exemplary visual field representation generated by an embodiment of a visual field measurement system according to the present invention from a patient response. The visual field representation is a three-dimensional plot of contrast sensitivity 904 plotted across a two-dimensional visual field comprising an X axis 900 and a Y axis 902 demarcated in degrees. As previously described, a patient outlines visual field defects on a visual field test pattern displayed at a plurality of contrast sensitivities. Each of these outlined visual field defects is plotted on a two-dimensional plane defined by the contrast sensitivity at which the visual field defect was outlined by the patient. These creates a three-dimensional visual field representation 908 with great descriptive power.

Returning to FIG. 8, the tester generates 802 a statistical description of the patient response. A statistical description of the patient response is useful by a diagnostic tool to determine the severity of a visual field defect. A statistical description of a visual field defect is also useful for comparison of a visual field defect to historical data collected from the patient.

Figure 10:
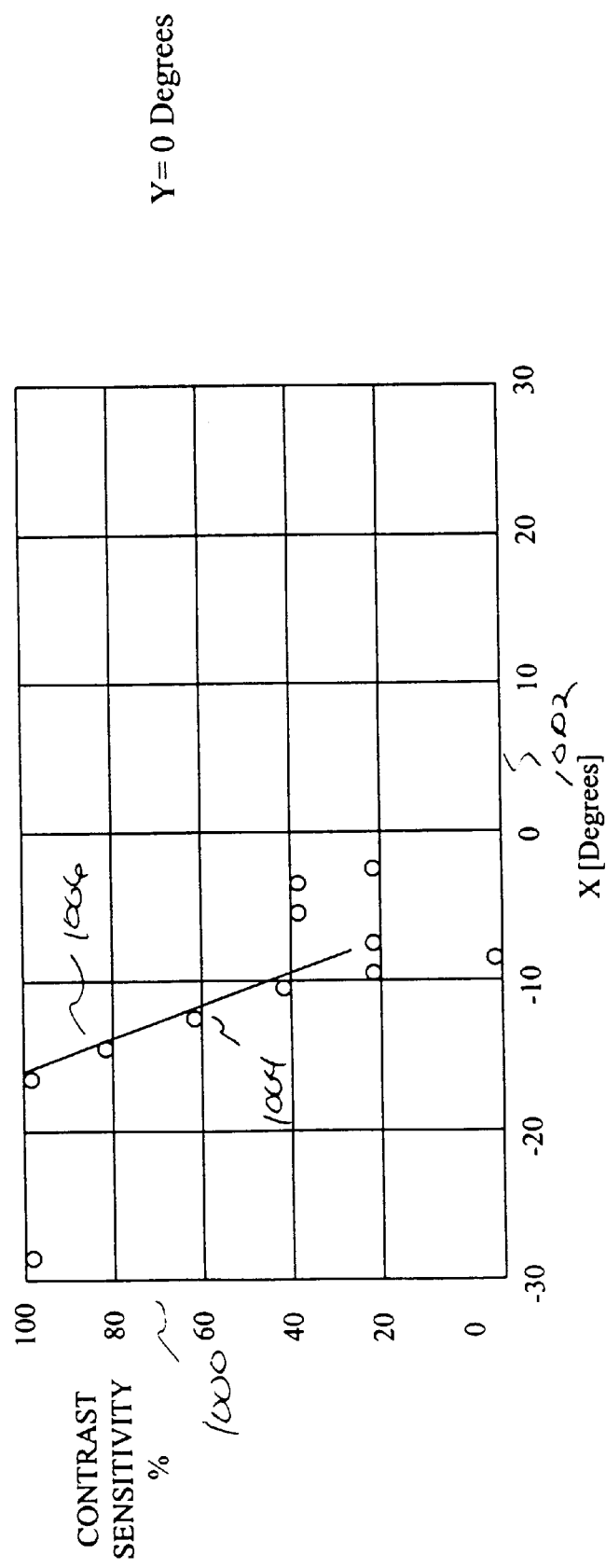
FIG. 10 is an exemplary output from an embodiment of a visual field measurement system according to the present invention illustrating the generation of a statistical description of a patient's response.

FIG. 10 is an exemplary output from an embodiment of a visual field measurement system according to the present invention illustrating the generation of a statistical description of a patient's response. In this example, the patient's response is transformed into a plot of retinal contrast sensitivity 1002 versus displacement along an X axis of the visual field. In this case, a defect in the visual field is shown by a decrease in contrast sensitivity 1004. A line 1006 generated through a linear regression process depicts the steepness of the decline in contrast sensitivity of the retina corresponding to the location of the visual field defect.

In another embodiment of a visual field measurement system according to the present invention, the visual field data is presented as a ratio between the loss of contrast sensitivity over degrees of visual field taken perpendicularly to the steepest or shallowest slope, expressed as a grade (% contrast sensitivity/degree).

Referring again to FIG. 9, in another embodiment of a visual field measurement system according to the present invention, a visual field defect is characterized by a ratio of an area of the visual field defect at a highest measured contrast sensitivity 914 versus an area of the visual field defect at a lowest measured contrast sensitivity 916.

Referring again to FIG. 8, statistical descriptions of patient's responses and visual field representations are used by the tester to track the progress of an ailment affecting the visual field. In a history 804 state, the tester generates time series of either statistical descriptions or visual field representations for use by a clinician in monitoring the progress of an ailment.

Visual field representations are used to create a diagnostic tool using Artificial Intelligence to diagnose a patient's ailments affecting the visual field. For example, patients suffering from macular degeneration experience a loss of vision because of impairments of the central retina and thus will have trouble seeing the visual field test pattern near the center fixation point. Since macular degeneration sufferers have peripheral vision, they would likely outline a central hole on the screen, and if they also had a relative visual field defect, they might trace an ever-smaller circle as the contrast of the visual field test pattern increased.

Referring again to FIG. 9, the visual field representation for a patient with "dry" macular degeneration is characterized by a peripheral area 910 of high contrast sensitivity. In the center of the visual field 912, the contrast sensitivity drops off significantly creating a hole in the visual field representation.

Figure 11:
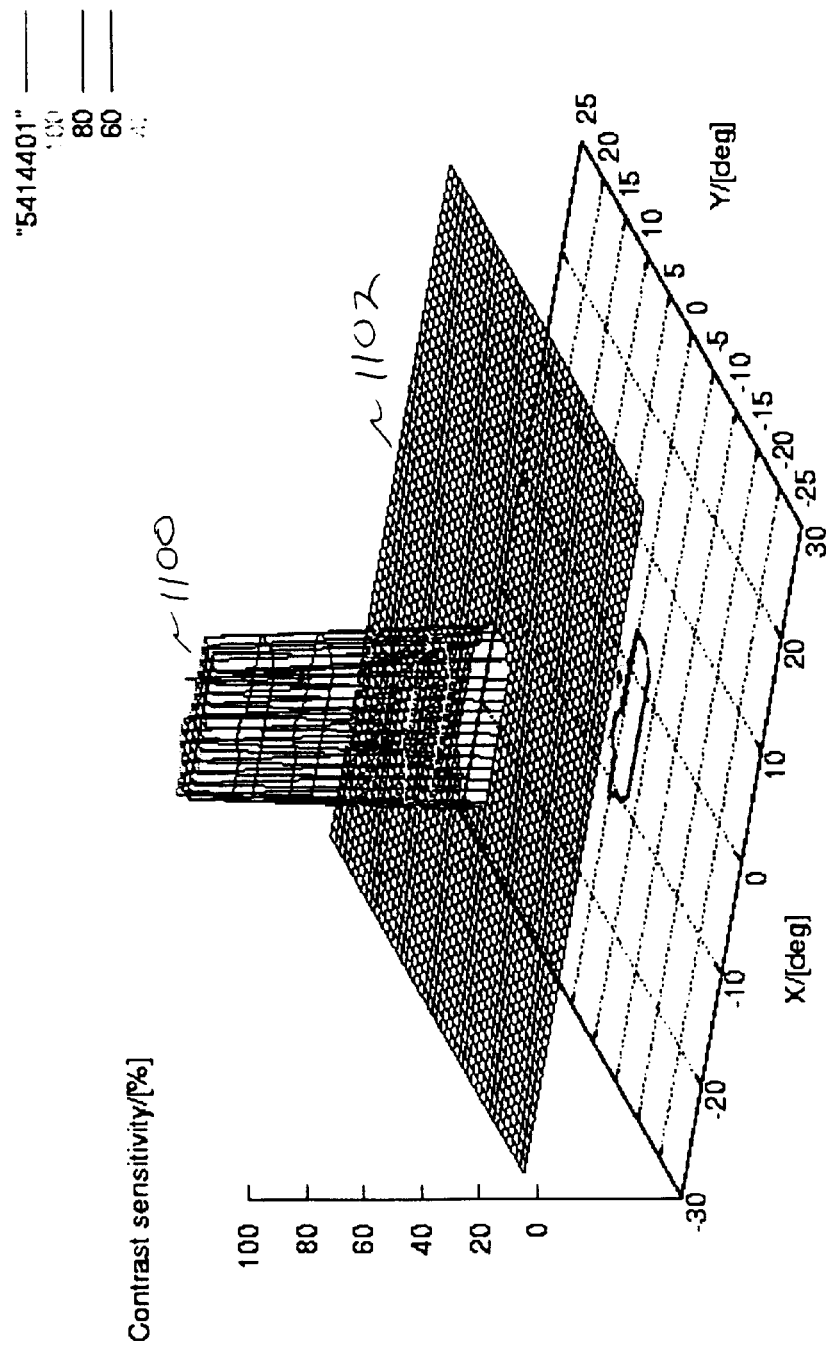
FIG. 11 is an exemplary visual field representation for a patient with glaucoma generated by an embodiment of a visual field measurement system according to the present invention.

FIG. 11 is an exemplary visual field representation for a patient with glaucoma generated by an embodiment of a visual field measurement system according to the present invention. A glaucoma patient is most likely to experience a loss of retinal sensitivity at the perimeter of the retina. Thus a glaucoma patient will outline a central area 1100 of high contrast sensitivity surrounded by an area 1102 of low contrast sensitivity.

The distinctive characteristics of visual field representations are used as the basis of a diagnostic tool employing pattern matching to determine a diagnosis from a visual field representation created from a patient's responses.

Figure 12:
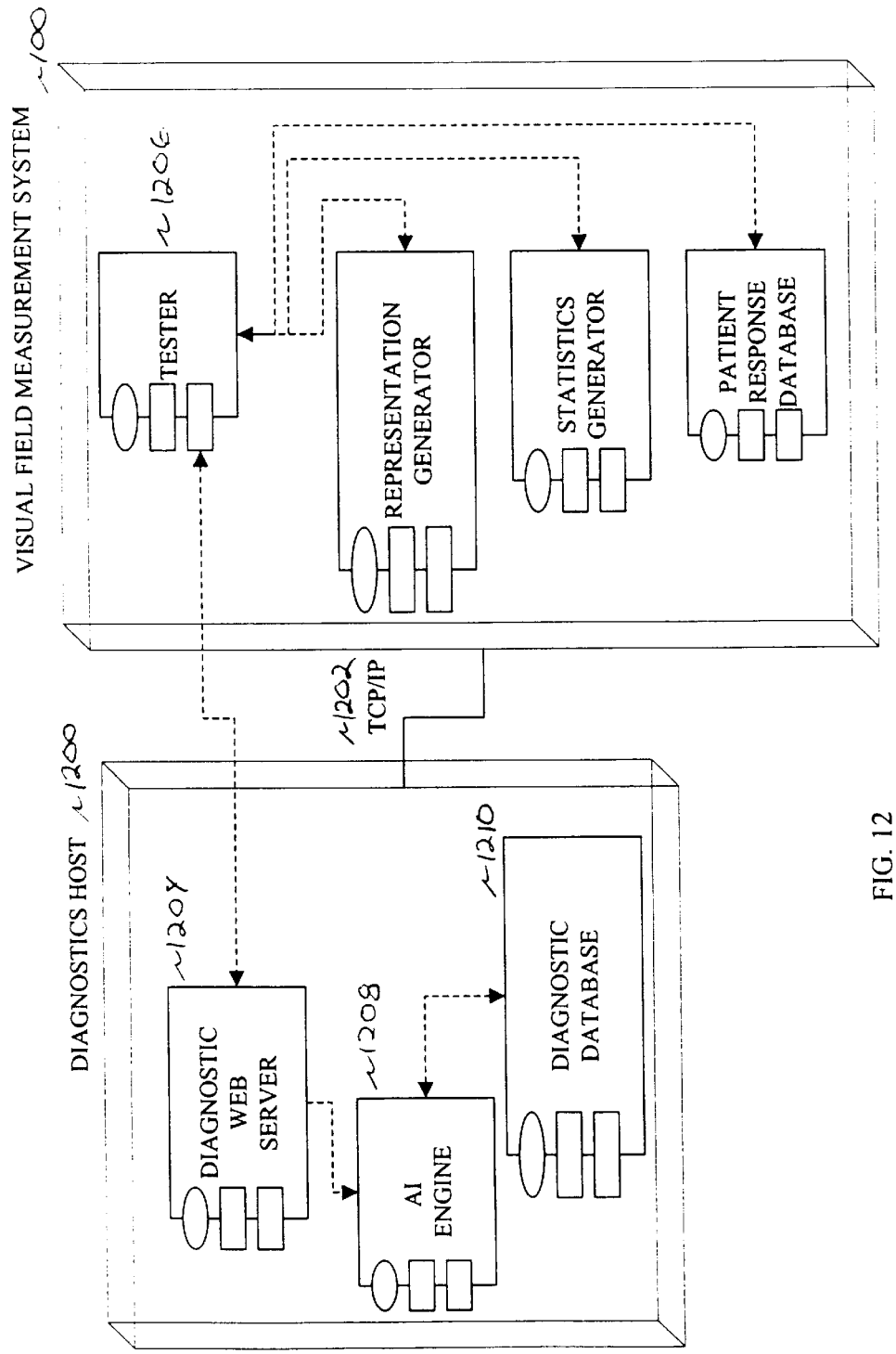
FIG. 12 is a deployment diagram of an embodiment of a distributed diagnostic system according to the present invention.

FIG. 12 is a deployment diagram of an embodiment of a distributed diagnostic system according to the present invention. A plurality of visual field measurement systems as exemplified by visual field measurement system 100 are operably coupled to a diagnostic host 1200 via a communications link 1202 adapted for communications using TCP/IP. The diagnostic host hosts a diagnostic Web server operably coupled to a previously described tester software module 1206 through the communications link. The diagnostic Web server is also operably coupled to an diagnostics generator such as an AI engine 1208. The AI engine is also operably coupled to a diagnostic database. The diagnostic database includes a set of visual field representations mapped to a set of diagnoses.

Figure 13:
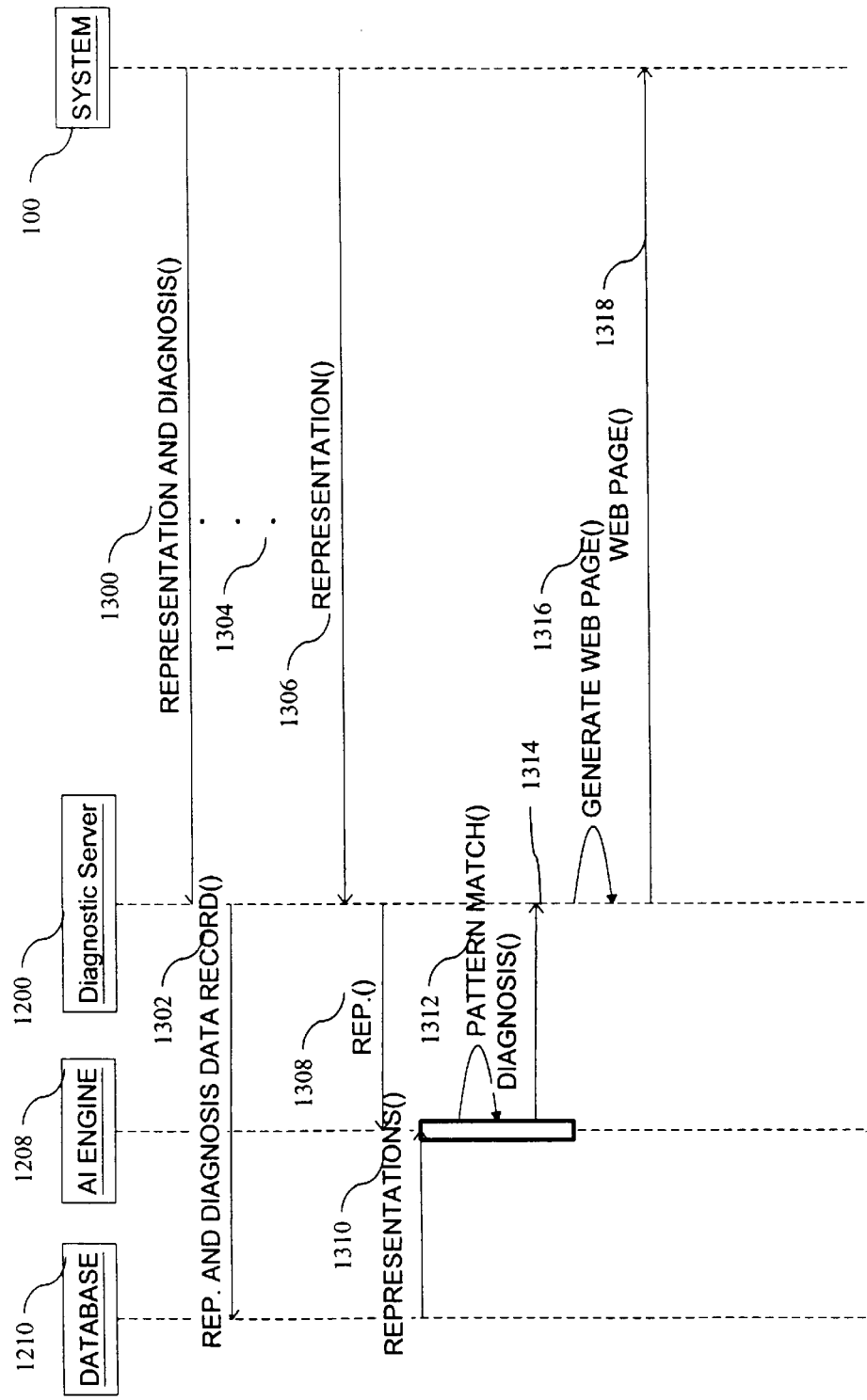
FIG. 13 is a sequence diagram of the operation of a distributed diagnostic system according to the present invention.

FIG. 13 is a sequence diagram of the operation of a distributed diagnostic system according to the present invention.

In operation, a visual field measurement system 100 performs a visual field measurement acquiring a patient's responses and generates a visual field representation as previously described. A clinician performs an independent analysis of the patient and generates a diagnosis with a high confidence factor. The clinician transmits the visual field representation and diagnosis 1300 to a diagnostic server 1200. The diagnostic server generates a database record 1302 correlating the visual field representation and the diagnosis and puts the data record in the diagnostic database 1210.

This process is repeated 1304, building a set of a set of visual field representations mapped to a set of diagnoses in the diagnostic database.

To determine a diagnosis, a visual field measurement system 100 performs a visual field measurement acquiring a patient's responses and generates a visual field representation as previously described.

The visual field measurement system transmits the visual field representation 1306 to the diagnostic server and the diagnostic server transmits the visual field representation 1308 to the AI engine.

The AI engine receives the visual field representation and gets the set of visual field representations mapped to a set of diagnoses from the diagnostic database. The AI engine searches the set of visual field representations for visual field representations with a high correlation to the received visual field representation using pattern matching techniques 1312. If a matching database visual field representation is found, the AI engine transmits a diagnosis 1314 associated with the database visual field to the diagnostics Web server.

The diagnostic Web server generates a diagnostic Web page 1318 using the diagnosis and transmits the diagnostic Web page to the visual field measurement system.

Figure 14:
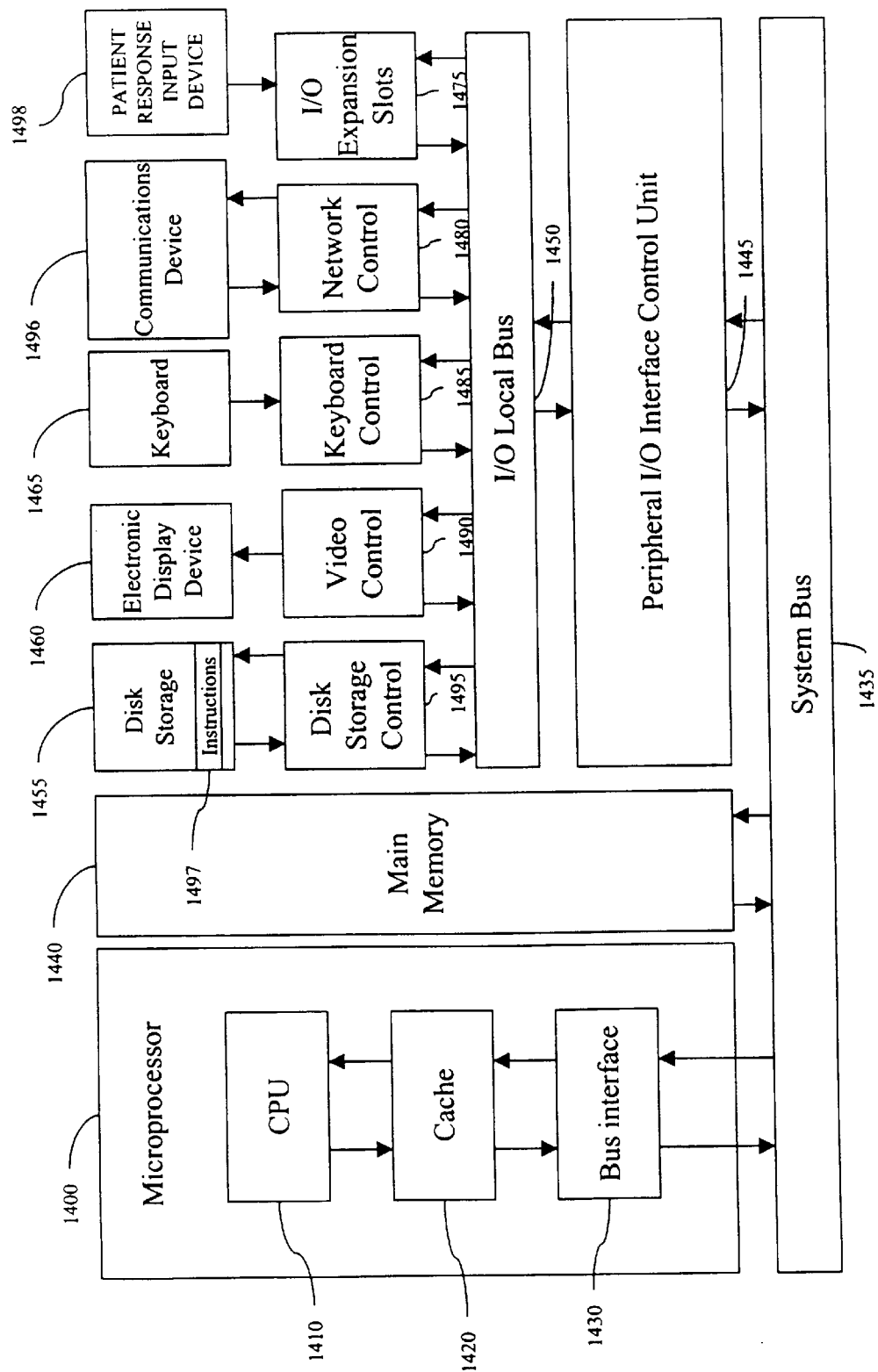
FIG. 14 is an architecture diagram for a general purpose computer suitable for use as a visual field measurement system according to the present invention.
Figures 15A, 15B, 15C, 15D:
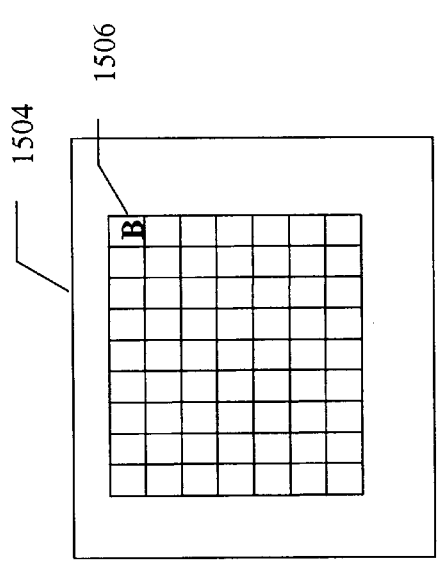
FIGS. 15a, 15b, 15c, and 15d are depictions of a visual field test patterns with peripheral fixation points in accordance with an exemplary embodiment of the present invention.

FIG. 14 is an architecture diagram for a general purpose computer suitable for use as a visual field measurement system according to the present invention. A microprocessor 1400, comprised of a Central Processing Unit (CPU) 1410, a memory cache 1420, and a bus interface 1430, is operably coupled a via system bus 1435 to a main memory 1440 and an I/O control unit 1445. The I/O interface control unit is operably coupled via an I/O local bus 1450 to a disk storage controller 1495, a video controller 1490, a keyboard controller 1485, a network controller 1480, and a I/O device controller 1475. The disk storage controller is operably coupled to a disk storage device 1455 for storage and retrieval of computer instructions 1497 and data. The video controller is operably coupled to an electronic display device 1460 for display of visual field test patterns to a patient. The keyboard controller is operably coupled to a keyboard 1465 for input of commands to the visual field measurement system. The network controller is operably coupled to a communications device 1496. The communications device is adapted to allow software objects hosted by the general purpose computer to communicate via a network with other software objects. The I/O device controller is operably coupled to a patient response input device 1498 for input of patient responses to the visual field test pattern.

Computer program instructions 1497 implementing software objects comprising a visual field measurement system are stored on the disk storage device until the microprocessor retrieves the computer program instructions and stores them in the main memory. The microprocessor then executes the computer program instructions stored in the main memory to instantiate a visual field measurement system.

Although this invention has been described in certain specific embodiments, many additional modifications and variations would be apparent to those skilled in the art. It is therefore to be understood that this invention may be practiced otherwise than as specifically described. Thus, the present embodiments of the invention should be considered in all respects as illustrative and not restrictive, the scope of the invention to be determined by claims supported by this application and the claim's equivalents rather than the foregoing description.

What is claimed is:

1. A method of measuring a patient's visual field, comprising:
   repeating steps a and b for a plurality of varying contrast levels and a plurality of corresponding patient response signals:
   a) presenting a visual field test pattern with a peripheral fixation point to the patient using an electronic display device, the visual field test pattern presented at a contrast level selected from the plurality of varying contrast levels;
   b) receiving a corresponding patient response signal; and
   generating a visual field representation using the plurality of contrast levels and the plurality of corresponding patient response signals.

2. The method of claim 1, wherein the peripheral fixation point is a variable peripheral fixation point.

3. The method of claim 1, wherein the visual field test pattern is a grid of substantially orthogonal lines.

4. The method of claim 3, wherein a grid spacing within the grid of substantially orthogonal lines is at least 1.0 arc minutes of the patient's visual field.

5. The method of claim 1, wherein the visual field representation is a three-dimensional graphical representation of the visual field.

6. The method of claim 1, wherein the visual field representation is a statistical description of the patient's visual field.

7. The method of claim 6, wherein the statistical description of the patient's visual field includes a ratio between the loss of contrast sensitivity over degrees of visual field taken perpendicularly to a steepest slope of visual field loss.

8. The method of claim 6, wherein the statistical description of the patient's visual field includes a ratio between the loss of contrast sensitivity over degrees of visual field taken perpendicularly to a shallowest slope of visual field loss.

9. The method of claim 6, wherein the statistical description of the patient's visual field includes a ratio of an area of the visual field defect at a highest measured contrast sensitivity versus an area of the visual field defect at a lowest measured contrast sensitivity.

10. The method of claim 1, the method further comprising:
    storing a time series of patient response signals for a patient; and
    using the time series of patient response signals to monitor the visual field in the patient.

11. The method of claim 1, the method further comprising:
    storing a set of a patient response signals for a known visual field defect cause; and
    comparing a patient's patient response signal to the set of patient response signals to determine the cause of the patient's visual field defects.

12. The method of claim 1, further comprising:
    presenting a cursor within the visual field test pattern; and
    updating the position of the cursor within the visual field test pattern using the patient response signal.

13. The method of claim 1, further comprising varying the presentation of the visual field test pattern while receiving the patient response signal.

14. The method of claim 1, wherein the visual field test patterns vary in color.

15. The method of claim 1, wherein the order of presentation of the visual field test patterns is random with respect to the varying contrast levels.

16. The method of claim 1, wherein the order of presentation of the plurality of visual field test patterns is according to the varying contrast levels.

17. A method of measuring a patient's visual field, comprising:
    repeating steps a and b for a plurality of selected contrast levels and a plurality of corresponding patient response signals:
    a) presenting an Amsler visual field test pattern including a peripheral fixation point at
    a selected contrast level to the patient using an electronic display device;
    b) receiving corresponding patient response signals from a patient input device operated by the patient;
    generating a three-dimensional graphical visual field representation using the plurality of selected contrast levels and the plurality of corresponding patient response signals.

18. An apparatus for measuring a patient's visual field using a visual field test pattern having a peripheral fixation point, comprising:
    an electronic visual field test pattern display device;
    a patient response input device;
    a visual field tester operably coupled to the visual field test pattern display device and the patient response input device; and
    a visual field representation generator operably coupled to the visual field tester.

19. The apparatus of claim 18, wherein the peripheral fixation point is a variable peripheral fixation point.

20. The apparatus of claim 18, wherein the visual field test pattern is a grid of substantially orthogonal lines.

21. The apparatus of claim 20, wherein a grid spacing within the grid of substantially orthogonal lines is at least 1.0 arc minutes of the patient's visual field.

22. The apparatus of claim 18, wherein the visual field representation is a three-dimensional graphical representation of the visual field.

23. The apparatus of claim 18, wherein the visual field representation includes a statistical description of the patient's visual field.

24. The apparatus of claim 23, wherein the statistical description of the patient's visual field includes a ratio between the loss of contrast sensitivity over degrees of visual field taken perpendicularly to a steepest slope of visual field loss.

25. The apparatus of claim 23, wherein the statistical description of the patient's visual field includes a ratio between the loss of contrast sensitivity over degrees of visual field taken perpendicularly to a shallowest slope of visual field loss.

26. The apparatus of claim 23, wherein the statistical description of the patient's visual field includes a ratio of an area of the visual field defect at a highest measured contrast sensitivity versus an area of the visual field defect at a lowest measured contrast sensitivity.

27. The apparatus of claim 18, the apparatus further comprising:
 a patient response database for storing a time series of patient response signals received from a patient using the patient input device; and
 a patient response history generator for monitoring the visual field in the patient using the time series of patient response signals.

28. The apparatus of claim 18, the apparatus further comprising:
 a patient response database for storing a set of of patient response signals received from patients using a patient input device; and
 a diagnostics generator for comparing a patient response signal to the set of patient response signals to determine the cause of the patient's visual field defects.

29. The apparatus of claim 18, wherein the visual test pattern further includes a cursor responsive to patient response signals received from the patient response input device.

30. The apparatus of claim 18, wherein the visual test pattern includes a plurality of visual field test patterns with varying contrast levels.

31. The apparatus of claim 30, wherein the order of presentation of the plurality of visual field test patterns is random with respect to the varying contrast levels.

32. The apparatus of claim 30, wherein the order of presentation of the plurality of visual field test patterns is according to the varying contrast levels.

33. The apparatus of claim 30, wherein the visual test patterns are presented in varying colors.

34. The apparatus of claim 18, wherein the patient response input device is a touch sensitive screen.

35. The apparatus of claim 18, wherein the patient response input device is a pointing device.

36. The apparatus of claim 18, wherein the tester is operably coupled to the electronic display device and the patient response input device through a communications network.

37. A method of measuring a patient's visual field, comprising:
 repeating steps a and b for a plurality of colors and a plurality of corresponding patient response signals:
  a) presenting a visual field test pattern including a fixation point to the patient using an electronic display device, the visual field test pattern presented in a color selected from the plurality of varying contrast levels;
  b) receiving a corresponding patient response signal; and
 generating a visual field representation using the plurality of colors and the plurality of corresponding patient response signals.

38. The method of claim 37, wherein the fixation point is a variable fixation point.

39. The method of claim 37, wherein the visual field test pattern is a grid of substantially orthogonal lines.

40. The method of claim 39, wherein a grid spacing within the grid of substantially orthogonal lines is at least 1.0 arc minutes of the patient's visual field.

41. The method of claim 37, wherein the visual field representation is a three-dimensional graphical representation of the visual field.

42. The method of claim 37, further comprising:
 presenting a cursor within the visual field test pattern; and
 updating the position of the cursor within the visual field test pattern using the patient response signal.

43. The method of claim 37, wherein the order of presentation of the visual field test patterns is random with respect to the colors.

44. The method of claim 37, wherein the order of presentation of the plurality of visual field test patterns is according to the colors.

* * * * *